United States Patent
Beck

(10) Patent No.: US 10,801,872 B1
(45) Date of Patent: Oct. 13, 2020

(54) METHANE MONITORING AND CONVERSION APPARATUS AND METHODS

(71) Applicant: Surface Solutions Inc., Grande Prairie (CA)

(72) Inventor: Michael Beck, Grande Prairie (CA)

(73) Assignee: Surface Solutions Inc., Grande Prairie (CA)

( * ) Notice: Subject to any disclaimer, the term of this patent is extended or adjusted under 35 U.S.C. 154(b) by 0 days.

(21) Appl. No.: 16/832,902

(22) Filed: Mar. 27, 2020

(30) Foreign Application Priority Data

Aug. 6, 2019 (CA) .................................. 3051376

(51) Int. Cl.
*G01F 15/00* (2006.01)
*G01F 7/00* (2006.01)
*G01N 33/00* (2006.01)

(52) U.S. Cl.
CPC .............. *G01F 15/002* (2013.01); *G01F 7/00* (2013.01); *G01F 15/003* (2013.01); *G01F 15/005* (2013.01); *G01N 33/004* (2013.01)

(58) Field of Classification Search
CPC ........ G01F 15/002; G01F 7/00; G01F 15/005; G01F 15/003; G01N 33/004
See application file for complete search history.

(56) References Cited

U.S. PATENT DOCUMENTS

| | | | |
|---|---|---|---|
| 3,805,610 A | 4/1974 | Jacobs | |
| 4,450,718 A | 5/1984 | Hartemink | |
| 4,497,202 A | 2/1985 | Mermelstein | |
| 4,542,650 A | 9/1985 | Renken et al. | |
| 4,800,754 A | 1/1989 | Korpi | |
| 5,020,373 A | 6/1991 | Kamiunten et al. | |
| 5,131,741 A | 7/1992 | Zweben | |
| 5,187,972 A | 2/1993 | DeFriez | |
| 5,297,427 A | 3/1994 | Shambayati | |
| 5,332,005 A | 7/1994 | Baan | |
| 5,357,793 A | 10/1994 | Jouwsma | |
| 5,445,035 A | 8/1995 | Delajoud | |
| 5,511,416 A | 4/1996 | Shambayati | |
| 5,563,335 A | 10/1996 | Howard | |
| 5,576,498 A | 11/1996 | Shambayati | |
| 5,750,892 A | 5/1998 | Huang et al. | |
| 5,837,903 A | 11/1998 | Weigand | |
| 5,861,546 A | 1/1999 | Sagi et al. | |

(Continued)

FOREIGN PATENT DOCUMENTS

| CA | 2325966 | | 5/2002 |
|---|---|---|---|
| CA | 2726154 | A1 | 3/2011 |

(Continued)

OTHER PUBLICATIONS

George, D.L. and Bowles, E.B. Effects of Flow Conditioning on Gas Measurement. Pipeline & Gas Journal 235.2 (Feb. 2008): 59-62,64-65. (Abstract).

(Continued)

*Primary Examiner* — Mischita L Henson
(74) *Attorney, Agent, or Firm* — Oyen Wiggs Green & Mutala LLP

(57) ABSTRACT

A system and method for monitoring and recording methane emissions from a source of methane. In some aspects, apparatus and methods are provided for converting the emitted methane to a different compound such as carbon dioxide.

16 Claims, 7 Drawing Sheets

(56) References Cited

U.S. PATENT DOCUMENTS

| | | | |
|---|---|---|---|
| 6,119,730 | A | 9/2000 | McMillan |
| 6,212,937 | B1 | 4/2001 | Hubert et al. |
| 6,275,284 | B1 | 8/2001 | Kiel et al. |
| 6,435,860 | B1 | 8/2002 | Brookshire et al. |
| 6,470,732 | B1 | 10/2002 | Breton |
| 6,611,319 | B2 | 8/2003 | Wang |
| 6,668,663 | B2 | 12/2003 | May et al. |
| 7,178,409 | B2 | 2/2007 | Olin et al. |
| 7,265,832 | B2 | 9/2007 | Montgomery et al. |
| 7,437,927 | B2 | 10/2008 | Yamada et al. |
| 7,454,984 | B1 | 11/2008 | Ross et al. |
| 7,466,399 | B2 | 12/2008 | Melnyk |
| 7,609,368 | B2 | 10/2009 | Melnyk |
| 7,650,783 | B2 | 1/2010 | Pape et al. |
| 7,911,591 | B2 | 3/2011 | Montgomery et al. |
| 7,966,971 | B2 | 6/2011 | Zimmerman |
| 8,794,082 | B2 | 8/2014 | Huang et al. |
| 9,062,536 | B2 | 6/2015 | Fischer et al. |
| 9,091,575 | B2 | 7/2015 | Adachi et al. |
| 9,612,144 | B2 | 4/2017 | Jaaskelainen |
| 9,625,356 | B2 | 4/2017 | Jenkins et al. |
| 10,029,290 | B2 | 7/2018 | Campanella et al. |
| 2008/0162085 | A1* | 7/2008 | Clayton ............. G05B 23/0262 702/188 |
| 2010/0235117 | A1 | 9/2010 | Melnyk et al. |
| 2013/0167666 | A1 | 7/2013 | Jenkins et al. |
| 2015/0211885 | A1 | 7/2015 | Rutherford et al. |
| 2016/0258797 | A1 | 9/2016 | Hartman et al. |
| 2016/0341593 | A1* | 11/2016 | Schweitzer ............... G01F 7/00 |
| 2017/0120191 | A1 | 5/2017 | Nurkowski et al. |
| 2018/0164137 | A1 | 6/2018 | Layher et al. |

FOREIGN PATENT DOCUMENTS

| | | |
|---|---|---|
| CA | 2899850 A1 | 8/2014 |
| CA | 2990691 A1 | 12/2016 |
| CN | 2916585 Y | 6/2007 |
| CN | 101726336 A | 6/2010 |
| CN | 201852604 U | 6/2011 |
| CN | 102116649 A | 7/2011 |
| CN | 202467894 U | 10/2012 |
| CN | 102156112 B | 1/2013 |
| CN | 203349876 U | 12/2013 |
| CN | 203364895 U | 12/2013 |
| CN | 203479342 U | 3/2014 |
| CN | 203572531 U | 4/2014 |
| CN | 104453981 A | 3/2015 |
| CN | 104806390 A | 7/2015 |
| CN | 204439181 U | 7/2015 |
| CN | 205002814 U | 1/2016 |
| CN | 205037932 U | 2/2016 |
| CN | 105452819 B | 11/2018 |
| CN | 105378441 B | 7/2019 |
| DE | 4216086 A1 | 11/1993 |
| EP | 2035821 B1 | 8/2014 |
| EP | 1798529 B1 | 8/2017 |
| FR | 2713362 A1 | 6/1995 |
| GB | 2212277 A | 7/1989 |
| JP | S5734492 A | 2/1982 |
| JP | S5734493 A | 2/1982 |
| JP | S5734494 A | 2/1982 |
| JP | S57149918 A2 | 9/1982 |
| JP | S608718 A | 1/1985 |
| JP | S6156938 A | 3/1986 |
| JP | H0349373 A | 3/1991 |
| JP | H0552622 A2 | 3/1993 |
| JP | H0835874 A | 2/1996 |
| JP | H08159830 A | 6/1996 |
| JP | H0989619 A | 4/1997 |
| JP | 4016474 A | 9/1999 |
| JP | 2000241218 A2 | 9/2000 |
| JP | 2000283820 A2 | 10/2000 |
| JP | 2001041798 A | 2/2001 |
| JP | 2001324368 A2 | 11/2001 |
| JP | 2003114142 A2 | 4/2003 |
| JP | 2003247876 A | 9/2003 |
| JP | 2004093175 A | 3/2004 |
| JP | 3734025 B2 | 1/2006 |
| JP | 3758033 B2 | 3/2006 |
| JP | 2007057452 A | 3/2007 |
| JP | 2007303899 A | 11/2007 |
| JP | 2008002864 A | 1/2008 |
| JP | 2008032501 A | 2/2008 |
| JP | 2009115504 A | 5/2009 |
| JP | 2009300403 A | 12/2009 |
| JP | 2010008165 A | 1/2010 |
| JP | 4531426 B2 | 8/2010 |
| JP | 4966526 B2 | 7/2012 |
| JP | 5108158 B2 | 12/2012 |
| JP | 5403165 B2 | 1/2014 |
| JP | 5557251 B2 | 7/2014 |
| JP | 5569383 B2 | 8/2014 |
| JP | 2014185861 A | 10/2014 |
| JP | 5816831 B2 | 11/2015 |
| JP | 2016109615 A | 6/2016 |
| KR | 20070022840 A | 2/2007 |
| KR | 20110006869 U | 7/2011 |
| KR | 101317630 B1 | 10/2013 |
| WO | 9508065 A1 | 3/1995 |
| WO | 97/11336 | 3/1997 |
| WO | 0060317 A1 | 10/2000 |
| WO | 2017/197517 A1 | 11/2017 |

OTHER PUBLICATIONS

Tauber, Tamás; Berta, Brigitta; Szabó, Zsolt; Kovács, József; Márialigeti, Károly; Tóth, Erika M. A simple and novel volumetric method to metre low gas flows from laboratory-scale bioreactors and its application on laboratory sludge digesters. Applied Microbiology and Biotechnology 90.4 (May 2011): 1453-61. (Abstract).

AER Interim Directive ID 2003-01, Jan. 30, 2003, Alberta Energy and Utilities Board (10 Pages).

* cited by examiner

METHANE MONITORING AND CONVERSION APPARATUS AND METHODS

CROSS-REFERENCE TO RELATED APPLICATIONS

This application claims priority to Canadian patent application No. 3051376 filed 6 Aug. 2019, the entirety of which is incorporated by reference herein for all purposes.

TECHNICAL FIELD

Some embodiments of the present invention relate to systems or methods for measuring venting, e.g. from a gas or oil well, glycol dehydrator tower, compressor seal, pneumatic control, or solution gas tank. Some embodiments of the present invention relate to systems or methods for logging the release of gas, e.g. from a gas or oil well, glycol dehydrator tower, compressor seal, pneumatic control, or solution gas tank. Some embodiments of the present invention relate to systems or methods for measuring the release of gas, e.g. from a gas or oil well, glycol dehydrator tower, compressor seal, pneumatic control, or solution gas tank. Some embodiments of the present invention relate to systems or methods for converting methane, e.g. released by a gas or oil well, glycol dehydrator tower, compressor seal, pneumatic control, or solution gas tank, to a different compound, for example carbon dioxide.

BACKGROUND

Methane ($CH_4$) is the main constituent of natural gas, and is widely recognized as a major greenhouse gas, i.e. a gas the emission of which contributes to the gradual increase in surface temperatures of the earth described as global warming. Regulators have an interest in reducing the amount of methane discharged into the environment.

One source of methane is wellhead venting of conventional oil and gas wells. For example, the Alberta Energy Regulator (AER) in Canada estimates that roughly 19% of methane emissions relating to the operations of the oil and gas industry in the province come from wellhead venting of methane. There are regulations in place to regulate wellhead venting in that province and in other jurisdictions. There is the possibility of further regulations being introduced in the future, for example a fee payable on the amount of methane emitted by an oil or gas well.

Options available for handling the discharge of methane from oil wells vary depending on the amount of methane being discharged. For example, where a sufficiently high level of methane is being released by a well, one option is to burn or "flare" the methane. At lower flow rates of methane, the emitted gas typically cannot be flared, and is instead vented to atmosphere.

When conventional oil wells are depleted, the wellbore must be sealed to ensure that harmful fluids, including methane, are not released into the surrounding environment. A primary concern is to minimize the release of methane into the environment after abandonment of the well.

When a depleted well is plugged, it is allowed to settle and off-gas for up to two months. At that time, the surface casing vent flow (SCVF) is tested. If there is no flow, the well can be cut-and-capped and abandoned. If surface casing vent flow (SCVF) is detected, the stabilized flow rate and stabilized shut-in pressure are recorded. The surface casing vent flow (SCVF) and stabilized shut-in pressure are obtained by shutting in the vent, allowing pressure to build and stabilize in the wellhead. The values of these parameters are used to determine whether the surface casing vent flow (SCVF) is serious or non-serious. If there is no flow, then the well can be cut, capped and buried.

After a wellhead shut-in pressure test, the vent pressure must be reduced prior to resuming flow measurement in order to prevent a pressure surge at the flow meter. Typically, a bleed valve is opened to bleed off the accumulated pressure to atmosphere.

Currently (according to AER directive 20) to identify wellhead venting, a hose is connected to the well, inserted into water, and the formation of bubbles is counted. If bubbles are observed, then an analog positive displacement meter or orifice meter may be used to measure the surface casing vent flow.

Positive displacement and orifice plate meters are commonly used to measure the flow of various oil and gas venting. Gas flow rates during wellhead venting can be very low. Conventional flow measurement technologies such as positive displacement and orifice meters are not designed to measure such low flow rates and can provide poor accuracy. Further, many well sites are located in remote areas and do not have access to amenities such as power.

Methane is also discharged in other contexts where it can be important to quantify the amount of methane being released and/or convert the released methane to a different compound. Examples of such contexts include glycol dehydrator towers, compressor seals, pneumatic controls, and solution gas tanks.

For example, glycol dehydrators are used to remove water from natural gas streams to prevent the formation of hydrates and corrosion in pipelines. In a glycol dehydrator tower, wet gas enters the tower and bubbles up through a lean glycol composition that absorbs moisture from the natural gas stream. The glycol can also absorb small amounts of methane and other hydrocarbons as part of this process, which can result in the generation of methane emissions when the glycol is regenerated.

Compressors are widely used in the oil and gas sector, for example to compress natural gas at various stages of transmission and processing. Compressor seals are provided for example as part of a reciprocating compressor rod. Over time, valves or other components of the compressor seal wear and this can result in the release of methane.

Oil and gas sites are often at remote locations and may not have access to power. Gas pressure from a well can be used to operate valves or other pneumatic controls at the site. When these valves or controls are used or opened, they may release gas, including methane.

Oil pumpjacks are used to pump emulsion into solution gas tanks. As oil enters the tank, a gas solution (including methane) is released and vented from the tank. The solution gas can rise to the top of the tank due to gravity because of the lower density of the solution gas, including methane, as compared to the emulsion that enters the tank.

These and other activities result in the release of methane to atmosphere. There is a general desire for improved apparatus, systems and methods for evaluating and monitoring wellhead venting. There is a general desire for improved apparatus, systems and methods for quantifying the amount of methane present in gases vented through wellhead venting, since the vented gas is not generally composed entirely of methane.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, a method for detecting methane emitted from a gas source is provided. A flow rate of gas released by the gas source is measured. A proportion of methane present in the gas is measured. The flow rate and/or volume of methane being released is determined based on both the measured flow rate and the measured proportion of methane present in the gas.

In some aspects, at least one of the measured flow rate, the measured proportion of methane present in the gas, the flow rate of methane being released, or the volume of methane being released during a specific period of time is measured.

In some aspects at least a portion of the methane present in the gas is converted to one or more other components. In some aspects, the methane is converted to carbon dioxide. In some aspects, the conversion of methane is carried out using catalytic conversion. In some aspects, the conversion of methane is carried out using thermal catalytic conversion.

In some aspects, the gas source is surface casing vent flow, an ethylene glycol purifier, a glycol dehydrator tower, a compressor seal, a pneumatic control, or a solution gas tank.

In one aspect, a system for detecting methane emitted from a gas source is provided. The system has a flow meter in fluid communication with the gas source for measuring a flow rate of gas released by the gas source and a methane detector in fluid communication with the gas source for measuring a proportion of methane present in the gas.

In some aspects, the system further has a memory for storing data pertaining to the measured flow rate and the measured proportion of methane.

In some aspects, the system further has a converter for converting methane to a different compound. The converter is in fluid communication with the gas source and is positioned downstream of the methane detector. In some aspects, the converter is a catalytic converter. In some aspects, the converter is a thermal catalytic converter. In some aspects, the converter is configured to convert methane into carbon dioxide.

In some aspects, the system is suitable for use with gas sources including surface casing vent flow, ethylene glycol purifiers, glycol dehydrator towers, compressor seals, pneumatic controls, or solution gas tanks.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Figure 1:
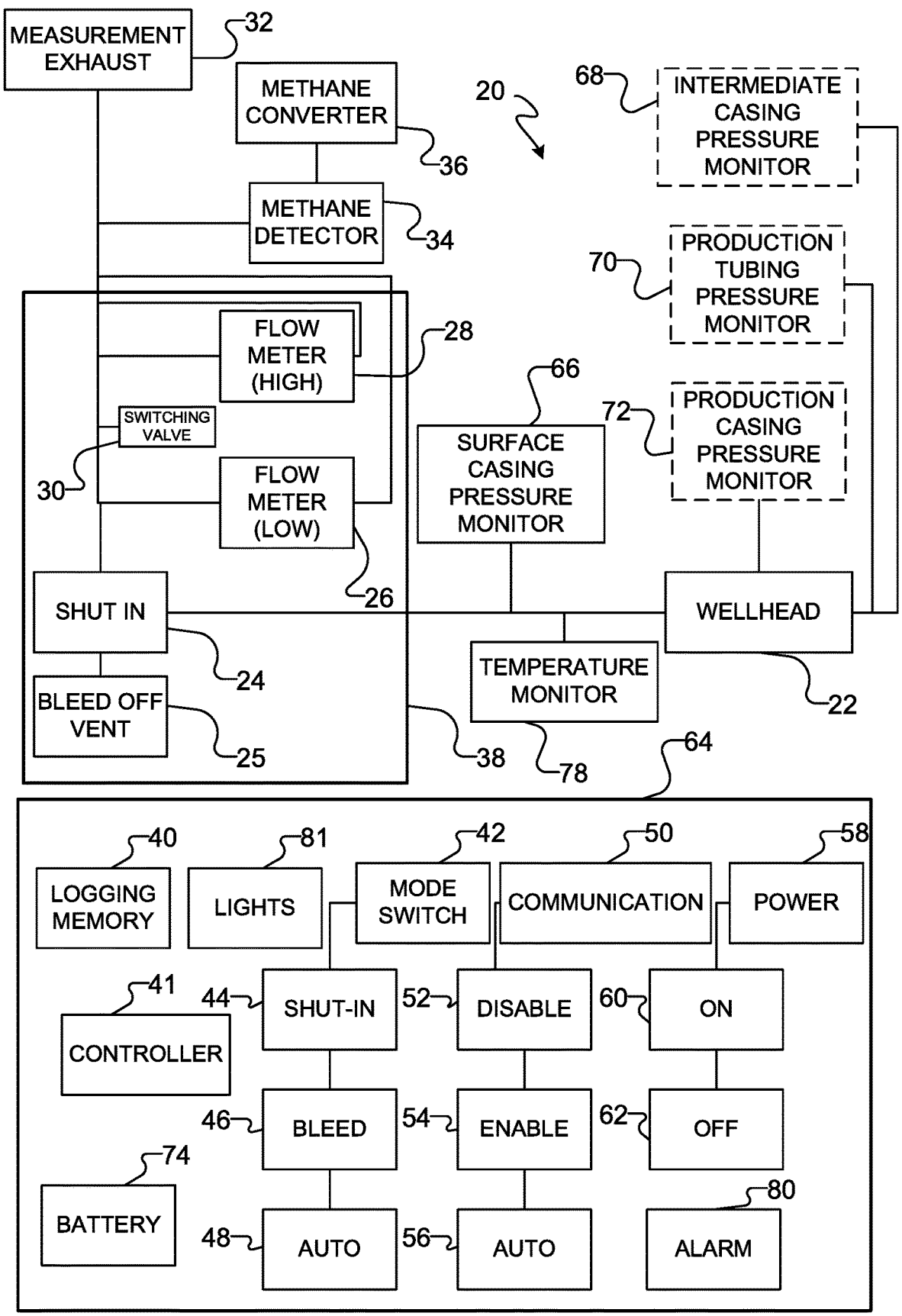
FIG. 1 shows an example embodiment of a methane monitoring, logging and conversion system according to an example embodiment for use in monitoring wellhead methane emissions.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

In one aspect, a vent gas methane data logger system is provided. The system has a data logging unit and a series of modular wellhead sensors and valves. The system can measure vent gas flow rate and methane composition to produce a totalized methane flow. The system can monitor one or a plurality of wellhead pressure transmitters. In some aspects, the system can measure up to four wellhead pressure transmitters. In some aspects, the data so obtained can be recorded using an on-board data logging hardware unit. In some aspects the data so obtained can be transmitted remotely using a cellphone, satellite or other communications unit. In some aspects, the system is modular, self-powered and communicates with the data logging hardware unit via wired or wireless means, e.g. a wireless transmitter or cable connection. In some aspects, the system is suitable for unattended operation. In some aspects, the system connects to an interface application.

In some aspects, the system is installed on a well to provide surface casing vent flow measurement. In some aspects, the system logs such measurements prior to abandonment of the well. In some aspects, the system is capable of measuring both a low flow rate range and a high flow rate range. In some aspects, the system selects the appropriate measuring flow rate range (e.g. low or high) based on the measured gas flow rate.

In some aspects, the flow meter is a laminar flow meter. In one aspect, an ultra-low-flow laminar flow meter is used to measure surface casing vent flow (SCVF). In some aspects, the laminar flow meter is provided as a pipe-mounted transmitter with an on-board battery and solar panel.

In some aspects, the system provides a vent shut-in function. In some aspects, the shut-in can be activated locally via any appropriate wired or wireless communication mechanism, e.g. Bluetooth. In some aspects, the shut-in can be activated remotely, e.g. via a cellphone or satellite signal, or via a web-based interface.

In some aspects, the system is self-powered using built-in batteries and/or a stand-mounted solar array. In some aspects, the system is not intended to be used with gas wells for which the surface casing vent flow contains hydrogen sulfide ($H_2S$) gas. In some aspects, the system has a mechanism for detecting the presence of hydrogen sulfide gas.

As used herein, a "low flow rate range" means a vent flow (e.g., surface casing vent flow) of approximately 0.03 to 6 $m^3$/day, including any value therebetween e.g. 0.04, 0.05, 0.06, 0.07, 0.08, 0.09, 0.1, 0.2, 0.3, 0.4, 0.5, 0.6, 0.7, 0.8, 0.9, 1, 1.2, 1.4, 1.6, 1.8, 2, 2.5, 3, 3.5, 4, 4.5, 5, or 5.5 $m^3$/day. As used herein, a "high flow rate range" means a vent flow (e.g., surface casing vent flow) of approximately 1.5 to 300 $m^3$/day or more, including any value therebetween e.g. 2, 3, 4, 5, 6, 7, 8, 9, 10, 20, 30, 40, 50, 75, 100, 125, 150, 175, 200, 225, 250 or 375 $m^3$/day or more. In some embodiments, the values may overlap for the low and high flow rate ranges, although in any specific embodiment, the lowest value of the low flow rate range may be selected to be a lower value than the lowest value measured in the high flow rate range.

In one embodiment, an exemplary methane emission data logger includes: a laminar flow meter; a data logger; and a methane sensor to quantify the percentage of methane in the vented gases. In some embodiments, the methane emission data logger further includes a catalyst to convert methane to a different gas, e.g. carbon dioxide. In some embodiments, the methane emission data logger further includes one or more pressure sensors, e.g. two, three, four, five, six, seven, eight, nine, ten or more pressure sensors.

In some embodiments, the system provides a vent shut-in and bleed-off function. These functions can be manually activated locally in some embodiments. These functions can be remotely activated in some embodiments, for example using a web-based interface.

In some embodiments, the system has local switches and indicators to facilitate operator control. In some embodiments, the system has an on-board data log storage with local wireless data log access.

In some embodiments, the flow meter measures the surface casing vent flow, and the methane sensor quantifies the amount of methane present in the flow to yield a determination of methane flow rate and/or a totalized methane flow from the well within a given period of time. In some embodiments, the system provides a determination of annual cumulative venting of methane for a well.

In one embodiment, the system has: a plurality of pressure sensors, a laminar flow meter, a datalogger memory storage with I/O control, a satellite web communication unit, a methane concentration meter, and a web-based interface for client login and control access.

In some aspects when operating within the low flow rate range, the system may measure the flow rate with an accuracy of ±1% of full scale output. In some aspects, when operating within the low flow rate range, the system samples and/or records data at a rate of up to 1 sample per second or less. In some aspects, sampling is conducted every 5 to 10 milliseconds. In some aspects, when operating within the high flow rate range, the system samples and/or records data at a minimum rate of 1 sample per day.

In some aspects, the user interface is provided with status LEDs for indicating power, Bluetooth, communication, or an error.

In some aspects, the system has a built-in battery and charge controller. In some aspects, the system is provided with a solar panel. In some aspects, the system is provided with a tripod-mounted solar panel.

In some aspects, the system or select components of the system are contained within a weather resistant case. In some aspects, the pressure monitor is a modular component that is wellhead mounted with a transmitter, on-board battery and solar panel.

In some aspects, the methane detector is provided as a modular component that is contained within a weather resistant case with an on-board battery and solar panel.

One example embodiment of a methane emission measuring, logging and conversion system 20 for use at a wellhead is illustrated in FIG. 1. System 20 is used to monitor, record and catalytically convert methane being released from a wellhead 22.

System 20 has a shut-in valve 24 connected to the wellhead 22. In some embodiments, shut-in valve 24 connects to a bleed off vent 25.

Shut-in valve 24 can be configured so gases being vented from wellhead 22 pass through a low flow range flow meter 26 or a high flow range flow meter 28, or pass directly to a measurement exhaust 32. A flow meter can be a laminar flow meter, thermal mass flow meter, optical flow meter, ultrasonic flow meter, or other suitable type of flow meter. In some embodiments, low flow range flow meter 26 and high flow range flow meter 28 are the same type of flow meter, e.g. laminar flow meters, and the range of the two flow meters is different. In one example embodiment, both low flow range flow meter 26 and high flow range flow meter 28 have a 200:1 turndown ratio, so that e.g. low flow range flow meter 26 can detect flow rates in the range of 0.03 to 6 $m^3$/day, and high flow range flow meter 28 can detect flow rates in the range of 2 to 300 $m^3$/day, to yield an accurate calibration range of 0.03-300 $m^3$/day of gas flow. In some embodiments, a third flow meter could be used with a different calibration, e.g. in the range of 3 to 600 $m^3$/day, to allow for even higher flow rate sources of gas flow to be measured. In some embodiments, low flow range flow meter 26 and high flow range flow meter 28 record measurements that can be used by system 20 to derive density data related to one or more components or compositions in a gas flow.

A switching valve 30 is provided to regulate the flow of gas through either low flow range flow meter 26 or high flow range flow meter 28. In some embodiments, switching valve 30 is controlled based on a measured flow rate of the gas flowing through shut-in 24, so that gas is directed to low flow range flow meter 26 when the gas flow rate is low or to high flow range flow meter 28 when the gas flow rate is high. In some embodiments, switching valve 30 is a four-way valve. In some embodiments, switching valve 30 can also direct the flow of gas through measurement exhaust 32, to bypass flow meters 26, 28, methane detector 34 and methane converter 36.

In some embodiments, the low flow range flow meter 26 is configured to accurately measure flow rates in the range of 0-2 $m^3$/day. In some embodiments, the high flow range flow meter 28 is configured to accurately measure flow rates in the range of 0-30 $m^3$/day.

When not being directed through bleed-off vent 25, gas flows through either of flow meters 26 or 28 or through a measurement exhaust 32 from which the gas is vented to atmosphere.

In some embodiments, a methane detector 34 is provided to determine the proportion of methane present in the gas being exhausted from system 20. In some embodiments, a methane converter 36 is provided to catalytically convert the methane present in the gas being exhausted to a different compound, to reduce the level of greenhouse gas emissions from wellhead 22, as described in greater detail below. In some embodiments, including the illustrated embodiment, methane detector 34 and/or methane converter 36 are provided on a line separate from measurement exhaust 32, so that gas is only passed through methane detector 34 and/or methane converter 36 when not being vented via measurement exhaust 32. This allows the avoidance of measurement errors, for example as could occur if pressure is built up within the system by shutting in shut-in 24 and then released via measurement exhaust 32.

Although methane detector 34 has been illustrated as being positioned downstream of flow meters 26, 28, in alternative embodiments methane detector 34 could be positioned upstream of flow meters 26, 28, or flow meters 26, 28 could be positioned downstream of methane converter 36. It is important that methane detector 34 be positioned upstream of methane converter 36 where used, as the proportion of methane present in emissions from gas source 22 could not be determined after the methane has been converted to another compound by methane converter 36.

In some embodiments, some or all of shut-in valve 24, bleed off vent 25, low flow range flow meter 26, high flow range flow meter 28 and/or switching valve 30 are contained within a weather proof enclosure or housing, schematically denoted as 38. Other components could optionally be also provided within weather proof enclosure 38.

In the illustrated embodiment, system 20 further includes a data logging memory 40. Data logging memory 40 can be used to record various measured parameters relating to wellhead 22 over time, for example a surface casing vent flow rate, the proportion of methane present in the gas being vented from wellhead 22, the surface casing pressure, intermediate casing pressure, production tubing pressure, production casing pressure, and the like. In alternative embodiments, rather than being provided with an on-board data storage unit like data logging memory 40, data could be transmitted by system 20 for storage on a remote data storage system. In some embodiments, data logging memory 40 is a local USB memory. In some embodiments, data logging memory 40 is a storage unit, for example, providing persistent storage. In some embodiments, the data storage unit 40 is configured to receive data, for example, from another component included in system 20 (e.g., flow meter (high) 28, flow meter (low) 26, surface casing pressure monitor 66, methane detector 34, intermediate casing pressure monitor 68, production tubing pressure monitor 70, production casing pressure monitor 72, temperature monitor 78, a sensor, a monitor, and/or other component).

In some embodiments, system 20 records and/or stores one or more logs in data storage unit 40 (e.g., data logging memory 40). For example, in some embodiments, system 20 receives data relating to errors or to the state of system 20 and/or a component of system 20, including for example the gas flow rate at any given time measured by low flow rate flow meter 26 or high flow rate meter 28 and the corresponding percentage of methane contained in that gas flow as determined by methane detector 34 at that corresponding time. Data logging memory 40 can also store a corresponding timestamp, so that changes in the flow rate and/or methane composition of the gas flow can be monitored and evaluated over time.

System 20 can record and/or store an error counter log and a system state log for each type of error data and/or for a combination of error data, for example. System 20 can process the data received before recording and/or storing the processed data or aspects of it, for example. Examples of the data logged include data relating to, encoding, and/or that can be used to derive same: high pressure, low pressure, high temperature, low temperature, motor stall events, notification(s) from alarm unit 80, system mode (e.g., hand-switch position), time (e.g., time measurement taken), pressure (e.g., surface casing pressure, intermediate casing pressure, production casing pressure), temperature (e.g., enclosure temperature, ambient temperature), gas flow rate, gas flow volume within a predetermined time period, methane percent or amount, battery voltage or battery level, and the like.

Figure 2:
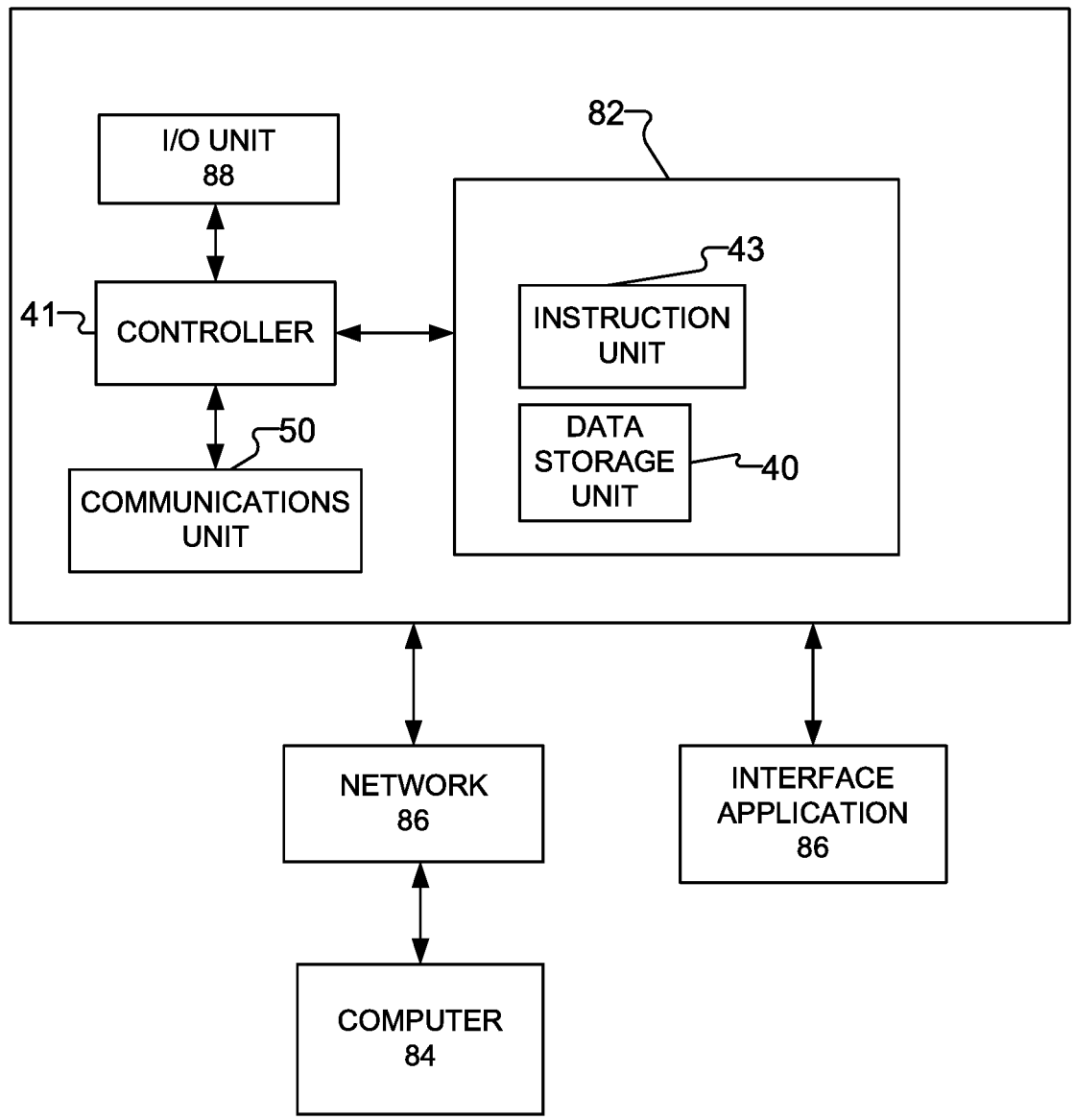
FIG. 2 shows an example embodiment of a control system for a methane monitoring, logging and conversion system according to an example embodiment.

System 20 further includes a controller 41 for controlling the operations of the various data monitoring, recording, communications and power functionalities of system 20. Controller 41 provides an interface for the software used by system 20. In some embodiments, for example, as shown in FIG. 2, controller 41 is a processor configured to execute instructions in an instructions unit 43, for example, in memory, to configure a storage device 82, for example, to perform the functions described herein. In some embodiments, the instructions unit 43 (e.g., memory), is included in a storage device 82 and configured to include a data transmission unit. In some embodiments, the data transmission unit is configured to receive data (e.g., from a data storage unit e.g., data logging memory 40, also referred to as storage unit 40), process the data, and/or transmit the data to another controller 41 included in system 20 and/or to a computer 84 connected to system 20 over a network 86. In some embodiments, system 40 is configured to connect to an interface application 86 directly (for example, via I/O unit 88) or, in some embodiments, over a network 86.

In some embodiments, system 20 further includes controls to allow an operator to regulate the operation of system 20. For example, in the illustrated embodiment, system 20 includes a mode switch control 42, to allow a user to switch between a shut-in mode 44, a bleed mode 46, or an automatic mode 48. In some embodiments, mode switch control 42 is included in an interface application 86, shown in FIG. 2.

In some embodiments, system 20 includes a communications unit 50 that allows for the wired or wireless transmission of data from system 20. In some embodiments, communications unit 50 is a radio communications unit, a Bluetooth communications unit, or other communications unit that uses other protocol(s) and/or other transmission frequencies. In some embodiments, system 20 includes controls that allow a user to disable 52, enable 54 or switch to automatic mode 56 the communication unit 50.

In some embodiments, system 20 includes a power switch 58 that allows a user to turn system 20 on 60 or off 62.

In some embodiments, some or all of data logging memory 40, controller 41, mode switch control 42, communications unit 50 and/or power switch 58 are contained within a weather proof enclosure or housing, illustrated schematically as 64. In some embodiments, system 20, optionally on housing 64, includes one or more local indicator lights 81 which indicate the mode of operation of system 20, the parameters that system 20 is monitoring, any malfunctions or errors in the operation of system 20, and/or the like.

In some embodiments, system 20 optionally includes one or more pressure sensors, to monitor the pressure at one or more locations. In the illustrated embodiment, a surface casing pressure monitor 66 is provided, to monitor pressure at the surface casing. In some embodiments, a production tubing pressure monitor 68, production casing pressure monitor 70 and/or an intermediate casing pressure monitor 72 are provided as part of system 20 to measure pressure at these locations. In some embodiments, the pressure sensors provided as part of system 20 are not integral to detecting, measuring, logging and/or converting methane, but are useful to meet other regulatory requirements.

In some embodiments, system 20 optionally includes one or more temperature monitors 78. The one or more temperature monitors 78 detect and/or measure temperature at a desired location. For example, in some embodiments, temperature monitor 78 detects and/or measures ambient temperature (e.g., temperature of an enclosure that the data logger can be situated in), temperature within system 20, temperature within a component of system 20 (e.g., housing 64 or housing 38), or environmental temperature outside system 20. In some embodiments, temperature monitor 78 detects and/or measures temperature during an automatic mode 48, bleed mode 46, or shut-in mode 44. In some embodiments, temperature monitor 78 records data indicative of or related to temperature detected and/or measured. In some embodiments, temperature monitor 78 provides data (e.g., temperature data) to an alarm unit 80.

In some embodiments, alarm unit 80 receives data from one or more components of system 20. In some embodiments, alarm unit 80 stores, records, transmits data, and/or actuates a notification related to and/or based on the data received. For example, in some embodiments, alarm unit 80 can receive temperature data from temperature monitor 78 and update an error counter log (e.g., stored locally and/or on a remote system/computer), and/or actuate a notification (e.g., message, alarm, sound, alert, etc.) based on the temperature data. For example, the notification can convey a low temperature alarm if the temperature data received from the temperature monitor 78 indicates and/or is processed by alarm unit 80 to indicate that an ambient temperature in system 20 (e.g., where a data logger is situated) is below a threshold value. In some embodiments, alarm unit 80 can receive pressure data from a pressure monitor (e.g., surface casing pressure monitor 66, production tubing pressure monitor 70, production casing pressure monitor 72, and intermediate casing pressure monitor 68), update an error counter log, and/or actuate a notification based on the pressure data. For example, the notification can convey a high pressure alarm if the pressure data indicates (e.g., before or after processing) that a pressure at a particular location (e.g., at surface casing, production tubing, production casing, other component of system 20, etc.) is above a threshold value.

In some embodiments, alarm unit 80 can receive and be triggered by data indicating that the flow rate of gas exiting the well exceeds the maximum threshold of the flow meter or the maximum threshold at which the flow meter can accurately measure flow rate (e.g. 300 m$^3$/day in some embodiments). In some embodiments, based on an alarm indicating that the flow rate of gas exiting the well exceeds the maximum threshold of the flow meter, a user of system 20 may elect not to accept or have regard to flow rate data measured after such an alarm point, and/or system 20 may direct the flow of gas through measurement exhaust 32. In some embodiments, alarm unit 80 can receive and be triggered by data indicating a low battery state, for example as the voltage drops below a predetermined value, an alarm condition can be generated to alert the user to consider replacing any batteries used to supply power to system 20 or installing new or additional solar panels to supply power to system 20.

In some embodiments, alarm unit 80 designates one or more datasets received with a status indicator, for example, denoting a critical alarm condition. In some embodiments, a critical alarm condition is activated or present (e.g., data received can be associated with a status indicator denoting a critical alarm condition based on the contents of the received data) the system 20 is set in a critical alarm state and the critical alarm condition is not removed until the critical alarm state is corrected. For example, alarm unit 80 can receive data from temperature monitor 78 that indicates an ambient temperature above or below a threshold value, store the ambient temperature data, associate the data with a critical alarm condition status indicator, and actuate a critical alarm state of system 20. Temperature monitor 78 can monitor the ambient temperature and transmit data indicating new temperature recordings to alarm unit 80. Alarm unit 80 can receive the new temperature recording data and, if this new temperature data is above or below a threshold value or difference from the previous temperature recording (e.g., the temperature recording data associated with the critical alarm condition), cancel the critical alarm condition associated with the recorded ambient temperature, and system 20 can exit the critical alarm state.

Figure 3:
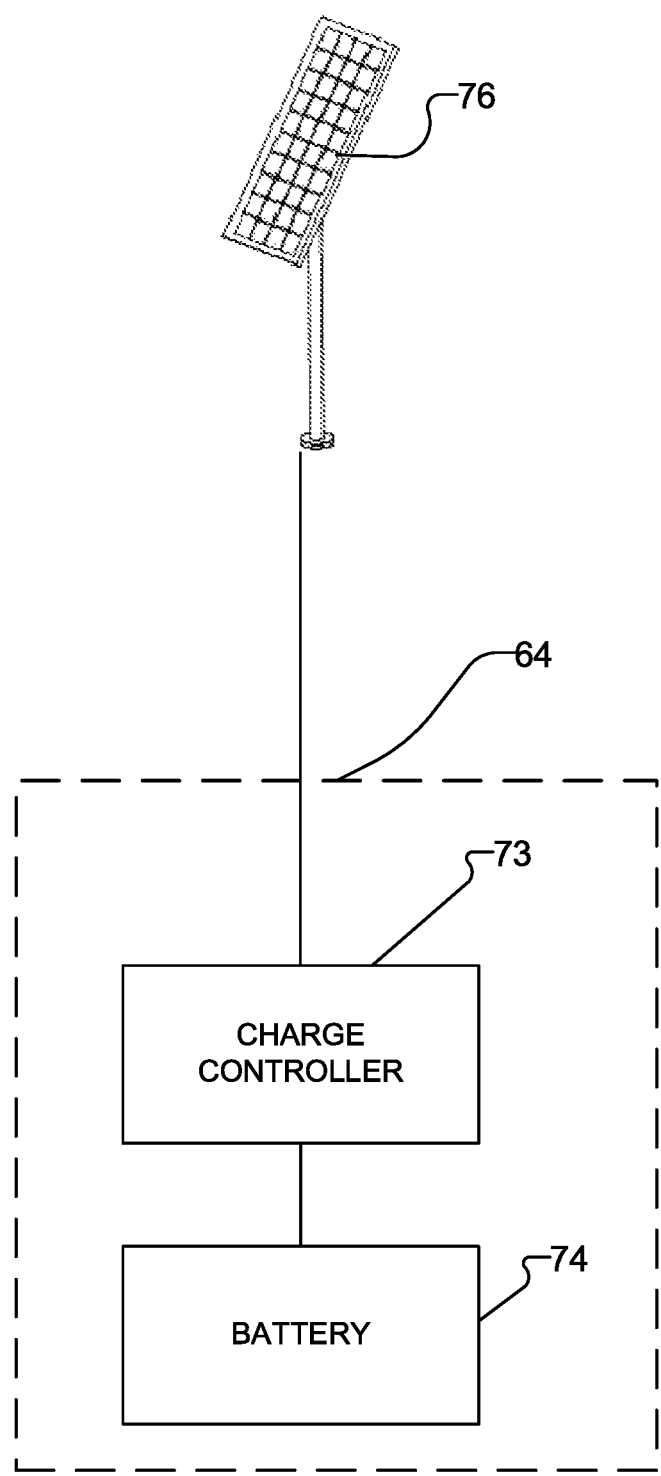
FIG. 3 shows an example embodiment of a power management system for a methane monitoring, logging and conversion system according to an example embodiment.

In some embodiments, a battery 74 is provided to power logging memory 40 and communications unit 50. In some embodiments, battery 74 is housed within housing 64. In some embodiments, battery 74 is housed external to housing 64. In some embodiments, a solar panel 76 is provided to charge battery 74. For example, FIG. 3 is a schematic diagram of an example power management system for a methane monitoring, logging and conversion system 20, according to some embodiments, having a solar panel 76 to supply power to battery 74 via a charge controller 73.

In some embodiments, the system 20 enters a low power mode or sleep state between measurements. In some embodiments, in the sleep state, the system cuts power to all instruments except the actuator used to actuate switching valve 30, flow meters 26, 28, and communications unit 50. When system 20 is taking measurements, the controller 68 powers the necessary sensors, takes updated measurements, sends the new readings to the communications unit 50 and saves a log of the updated values to the logging memory 40. In some embodiments, logging memory 40 is a local USB memory. After these steps have been completed, system 20 returns to the sleep state. In some embodiments, the wake period during which measurements are taken is approximately 15 seconds and the sleep cycle is approximately 45 seconds, so that the sleep interval or period covered by each sleep-wake cycle is approximately 1 minute.

In one example embodiment, when system 20 is in automatic mode 48, the system 20 will initially direct the flow of venting gases to high flow range flow meter 28. If it is determined that the flow rate of the vented gases is below a predetermined level, then the system 20 will actuate switching valve 30 to direct the flow of vented gases to low flow range meter 26. In some embodiments, the predetermined level below which the flow of vented gases is directed to low flow range meter 26 is less than about 6 m$^3$/day, including any lower value, e.g. 5.5, 5.0, 4.5, 4.0, 3.5, 3.0, 2.5, 2.0, 1.5 or 1.0 m$^3$/day.

In some embodiments, if bleed mode 46 is activated, the flow of vented gases will be directed directly to bleed off vent 25, bypassing flow meters 26, 28 and methane detector 34. In some embodiments, in the event of a loss of power, system 20 will use a back-up power source to direct flow directly to bleed off vent 25, bypassing flow meters 26, 28 and methane detector 34. In alternative embodiments, the flow of gas could be directed to measurement exhaust 32 to bypass flow meters 26, 28, methane detector 34 and methane converter 36.

In some embodiments, when shut-in mode 44 is activated, the surface casing vent line will be shut in to allow pressure to build up in the surface casing vent. In some embodiments, during operation in shut-in mode 44, system 20 continues to record such data as pressure measured by pressure monitors 66, 68, 70 and 72.

In some embodiments, a remote bleed function is provided. The remote bleed function works in the same way as bleed mode 46, but is activated remotely, e.g. using a web-based interface. The remote bleed function can be activated by a remote computer, for example. In some embodiments, the system must be operating in automatic mode 48 in order for the remote bleed function to be used.

In some embodiments, a high speed logging function is provided. The high speed logging function is used to identify a level of gas flow equivalent to the flow of bubbles breaking the water surface in a bubble test as is currently used to measure gas flow. For example, AER Directive 20 states that any well that has a gas flow rate that exhibits any bubble flow within a ten minute period cannot be cut-and-capped. Accordingly, in embodiments intended to replace the use of a conventional bubble test, system 20 must be able to measure very low gas flows even if such flow is sporadic, e.g. equivalent to the production of a bubble every seven minutes. A bubble popping event takes less than one second to occur, so to accurately characterize such wells, measurements must be made and recorded at least every second. For example, a digital laminar flow meter is able to take measurements on a millisecond timescale. In some embodiments, in high speed logging mode, a sample is taken every 5 to 10 milliseconds, including e.g. every 6, 7, 8 or 9 milliseconds.

In some example embodiments, the default logging duration is ten minutes. In some embodiments, measurements are logged once per minute.

In some embodiments, methane converter 36 is a thermal catalytic converter, for example as described in Canadian patent No. 2325966, which is incorporated by reference in its entirety herein. In some embodiments, a plurality of methane converter units are used to provide methane converter 36, e.g. two, three, four, five or more methane converter units, depending on the rate of methane being released. In some embodiments, the volume of methane converted to carbon dioxide by methane converter 36 is measured by methane detector 34, to allow a user of system 20 to apply for any relevant government credits or benefits relating to the amount of methane diverted from entering the atmosphere.

In alternative embodiments, methane converter 36 is any suitable type of converter, for example a catalytic converter, for example, a converter using an oxidation catalyst; a dual-bed catalytic converter; a three-way catalytic converter; a catalytic converter that uses an oxidation catalyst and a reduction catalyst; converter with a palladium or platinum face; and/or other catalytic converter.

In some embodiments, system 20 includes one or more methane converters 36.

The methane converters 36 can operate in sequence, for example, with an output of a first methane converter 36 provided as one or more input streams to one or more subsequent methane converters 36 and so on. In some embodiments, the sequence and/or identity of the one or more methane converters 36 can help minimize the amount of one or more gases (e.g., methane) released into the atmosphere from a gas-emitting system such as a wellbore.

Figure 4:
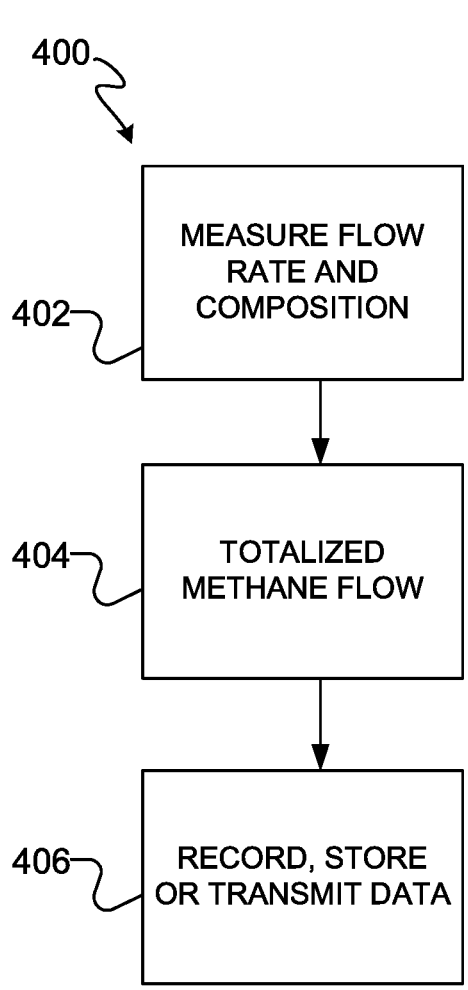
FIG. 4 shows a flow diagram of an example embodiment of a process for measuring gas flow rate and methane composition according to an example embodiment.

FIG. 4 is an example flow diagram illustrating an example process 400 for methane detection using system 20, according to some embodiments. At 402, system 20 is configured to measure vent gas flow rate from either of low flow rate flow meter 26 or high flow rate flow meter 28. The proportion of methane present in the vent gas is measured by methane detector 34. System 20 is configured to measure or generate a methane composition data value based on the vent gas flow rate. At 404, system 20 is configured to generate totalized methane flow data based on the vent gas flow rate and the methane composition data value obtained at 402. For example, the totalized methane flow data can be data representing an amount of methane flow from the well head per volume or per unit time of gas flow from the well head. At 406, system 20 is configured to record, store, and/or transmit data such as data derived from or indicating the totalized methane flow rate, vent gas flow rate, and/or methane composition. For example, system 20 at data storage unit 40 (e.g., data logging memory 40) is configured to store data, for example, as a log.

Figure 5:
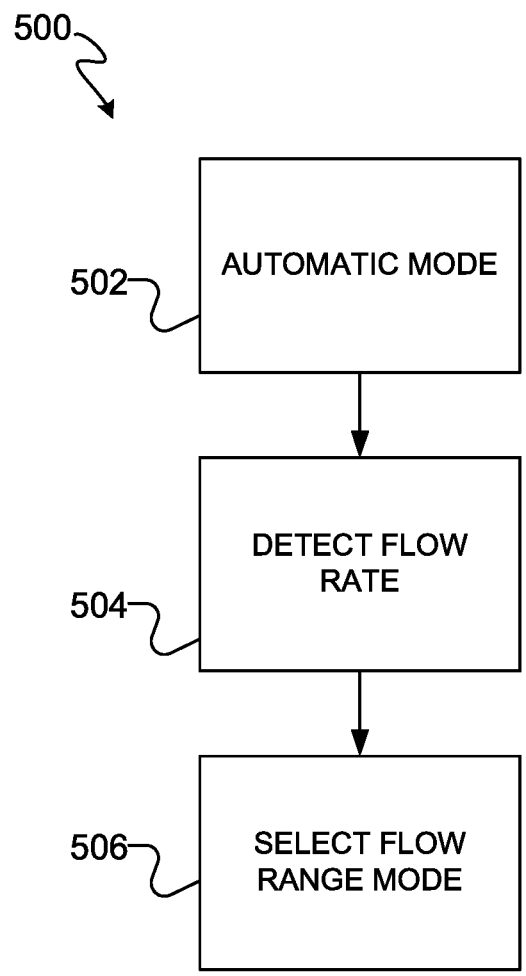
FIG. 5 shows a flow diagram of an example embodiment of a process for selecting a flow rate range mode based on a detected gas flow rate.

FIG. 5 is an example flow diagram of an example process 500 for methane detection using system 20 installed at a vent (e.g., at a well-head), according to some embodiments. In some embodiments, step 402 includes steps 502, 504, and 506.

At 502, system 20 enters automatic mode 48 where system 20 can initially enter a high flow rate detection mode. For example, in some embodiments, in the high flow rate detection mode, a switching valve 30 is configured so that vent gas is directed to high flow range flow meter 28.

At 504, system 20 is configured to detect a vent gas flow rate of gas from the vent using a sensor, e.g., a laminar flow meter. For example, the vent gas flow rate can be detected at one or more values or to be within a range of values.

At 506, system 20 is configured to select a flow rate range mode based on the detected vent gas flow rate. If system 20 (e.g., using laminar flow meter) detected a low flow rate, system 20 is configured to enter a mode that detects flow rates within a low flow rate range using low flow rate flow meter 26. For example, if system 20 (e.g., using high flow range flow meter 28) detected a low flow rate, switching valve 30 is configured to direct gas to low flow range flow meter 26. During operation or at step 504, if system 20 detects a high flow rate, system 20 is configured to enter a mode that detects flow rates within a high flow rate range. For example, if system 20 (e.g., using laminar flow meter) detected a high flow rate, switching valve 30 is configured to direct the flow of gas through a high flow range flow meter 28 so that gas is directed to high flow range flow meter 28 when the gas flow rate is high. In some embodiments, system 20 switches between a high flow rate detection mode and low flow rate detection mode one or more times, for example, based on changing or fluctuating flow rates of gas from the vent.

As gas flow rate is being measured by either of flow meters 26, 28, system 20 can then take one or more measurements using monitor(s) and/or sensor(s) and data storage unit 40 can record and/or store same.

In some embodiments, system 20 at alarm unit 80 is configured to trigger a notification (e.g., an alarm) based on a predetermined vent gas flow rate or other desired parameter. For example, if the vent gas flow rate is above a threshold value, alarm unit 80 is configured to trigger a notification indicating that a vent flow (e.g., surface casing vent flow) is serious. If the the gas flow rate is below a threshold value, alarm unit 80 can be configured to trigger a notification indicating that a vent flow (e.g., surface casing vent flow) is non-serious or within acceptable operating parameters for flow meters 26, 28, for example.

Figure 6:
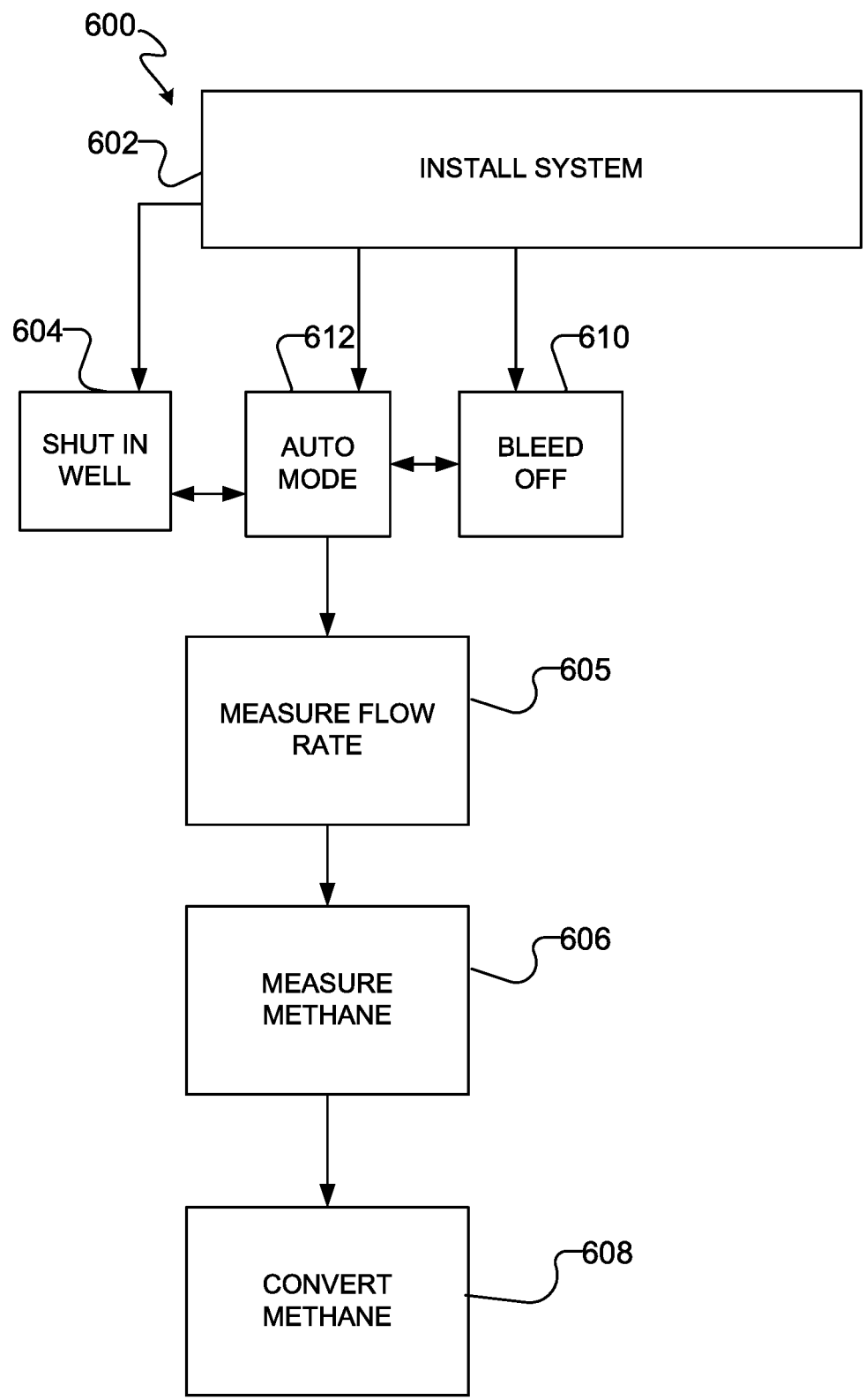
FIG. 6 shows a flow diagram of an example embodiment of a process for measuring and converting methane in different modes according to an example embodiment.

FIG. 6 is an example flow diagram of an example process 600 for operating system 20, according to some embodiments. As shown in FIG. 1, in some embodiments, system 20 is configured to operate in at least a shut-in mode 44, bleed off mode 46, and automatic mode 48.

At 602, system 20 is installed at a vent, e.g. a wellhead.

System 20 is configured to enter and/or exit a shut-in mode 44 at 604, bleed off mode 46 at 610, and automatic mode 48 at 612. For example, a user can engage with a mode switch control 42 to toggle system 20 between a shut-in mode 44, bleed off mode 46, and automatic mode 48. In some embodiments, system 20 is configured to allow for remote control when in the automatic mode 48. In some embodiments, system 20 is configured to enter a sleep mode, e.g. to conserve battery power. When the system is switched to a different mode from sleep mode, system 20 may take a period of time, such as one to two sleep cycles (e.g., 1-2 minutes) for the switch position to be acknowledged by the controller. When the system is in sleep mode, system 20 may wake up only to record measurements and then return to sleep, for example taking and recording a measurement every 1-2 minutes, to minimize the amount of power consumed by system 20.

At 604, system 20 is configured to enter a shut-in mode 44 and shut-in the well.

When system 20 is in shut-in mode 44, in some embodiments, data storage unit 40 is configured to record measurements taken from surface casing pressure monitor 66, intermediate casing pressure monitor 68, production casing pressure monitor 72, and temperature monitor 78 (e.g., that can measure temperature within enclosure 38).

At 610, e.g. as may occur upon loss of power or system failure, system 20 is configured to direct the flow of gas to a bleed off vent 25 to exit system 20, bypassing flow meters 26, 28 and methane detector 34 and/or methane converter 36. Further, in some embodiments, data storage unit 40 is configured to record timestamp data (e.g., denoting a time that one or more measurements are taken or that the mode in which system 20 is operating is changed). In alternative embodiments, rather than directing the flow of gas to bleed off vent 25, gas could be directed to measurement exhaust 32 to bypass flow meters 26, 28, methane detector 34 and methane converter 36.

At 612, system 20 is configured to enter an automatic mode 48. In automatic mode 48, system 20, for example, at data storage unit 40, is configured to log a measurement or set of measurements. Such logging can be performed once per minute, for example. In some embodiments, system 20 can enter a high speed logging function. When system 20 is in automatic mode 48, in some embodiments, data storage unit 40 is configured to record measurements taken from surface casing pressure monitor 66, intermediate casing pressure monitor 68, production casing pressure monitor 72, temperature monitor 78 (e.g., that can measure temperature within enclosure 38), flow meter (high) 28, and/or flow meter (low) 26. Further, in some embodiments, data storage unit 40 is configured to record timestamp data (e.g., denoting a time that one or more measurements are taken).

In some embodiments, system 20 is configured to enter into a high speed logging function. In a high speed logging function, system 20 is configured to take measurements at one or more monitors or sensors at a higher frequency. The frequency can be approximately seven readings per second, for example, or more, with measurements being made and recorded on a millisecond timescale. For example, the measurements can be taken using flow meter (high) 28 and/or flow meter (low) 26, and timestamp data can also be recorded. In some embodiments, system 20 does not enter sleep mode when it is in high speed logging mode.

At 606, in automatic mode 48, system 20, using methane detector 34, is configured to monitor, detect, and/or measure one or more properties of component(s) from the vent, for example, gas flow rate at 605 and/or methane composition/amount at 606.

At 608, after methane composition and flow rate of the vent gas have been measured, system 20, using methane converter 36, is configured to catalytically convert methane present in gas being exhausted from a vent to a different compound, to reduce the level of greenhouse gas emissions, for example, from wellhead 22. For example, methane detector 34 can be used to measure or quantify a percentage of methane contained in a gas flow from a vent, and methane converter 36 can convert one or more components of that gas flow (e.g., methane) to one or more other compounds, for example carbon dioxide.

In some embodiments, methane converter 34 catalytically converts methane to a different compound without system 20 using methane detector 34 to detect methane. In some embodiments, methane converter 36 catalytically converts methane to a different compound following detection or measurement of methane amount or composition by methane detector 34.

At 610, in bleed-off mode 46, system 20 passes gas through bleed off vent 25. For example, if a pressure monitor (e.g., 66, 68, 70, or 72) detects or measures a pressure above a threshold value, in some embodiments, system 20 is configured to enter bleed-off mode at 610 by directing the flow of gas through bleed off vent 25. In some embodiments, alarm 80 is triggered if bleed-off mode is entered.

Figure 7:
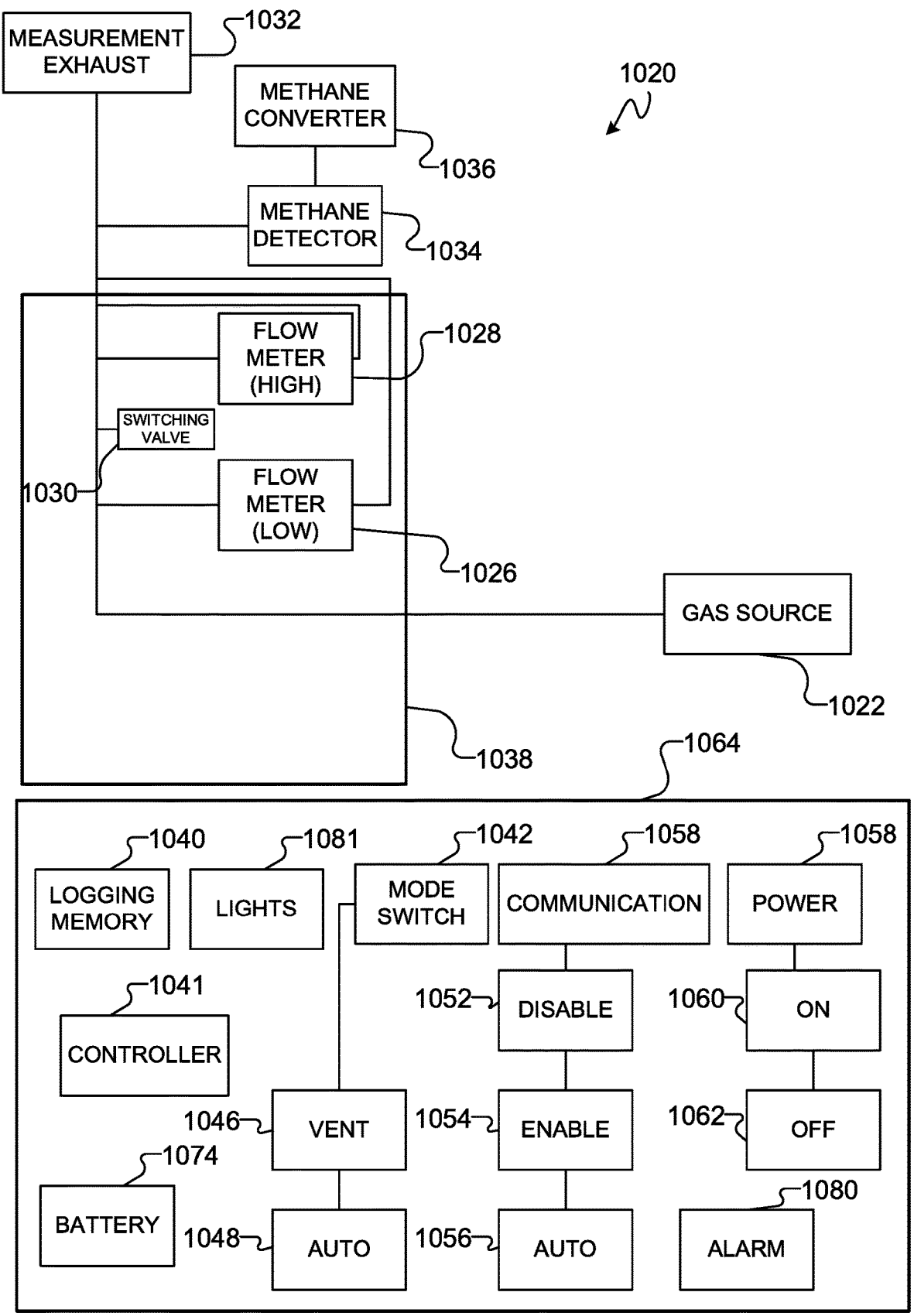
FIG. 7 shows an example embodiment of a methane monitoring, logging and conversion system according to an example embodiment.

FIG. 7 is an example embodiment of a system 1020 that is similar to system 20 and is operated in a similar manner, but which can be installed at a source of methane other than a wellhead. Components of system 1020 that are similar to components of system 20 are illustrated with reference numerals incremented by 1000, and are not further described herein. System 1020 is generally similar to system 20, except that components that are specific to the operation of the system at a wellhead (e.g. shut in 24, bleed off vent 25, pressure monitors 66, 68, 70, 72, and the like) are omitted.

System 1020 is installed at a gas source 1022 from which it is desired to monitor and/or convert methane emissions. Gas flows from gas source 1022 to system 20. In automatic mode 1048, gas flow is directed initially to high flow range flow meter 1028 and either gas flow rate is measured or, if high flow range flow meter 1028 determines that the flow rate from gas source 1022 is low, switching valve 1030 directs the flow of gas to low flow range flow meter 1026, which measures gas flow rate. At any time, if low flow range flow meter 1026 determines that gas flow rate is too high, switching valve 1030 directs the flow of gas to high flow range flow meter 1028.

Gas is also directed through a methane detector 1034, so that the proportion of methane in the gas flow can be determined. The data obtained from flow meters 1026, 1028 and methane detector 1034 can be used to determine the totalized flow of methane emitted by gas source 1022 in the same manner as described for system 20. Although methane detector 1034 has been illustrated as being positioned downstream of flow meters 1026, 1028, in alternative embodiments methane detector 1034 could be positioned upstream of flow meters 1026, 1028, or flow meters 1026, 1028 could be positioned downstream of methane converter 1036. It is important that methane detector 1034 be positioned upstream of methane converter 1036 where used, as the proportion of methane present in emissions from gas source 1022 could not be determined after the methane has been converted to another compound by methane converter 1036.

In some embodiments, after passing through methane detector 1034, gas is then directed to a methane converter 1036, so that the methane can be converted to a different compound, for example carbon dioxide. Any type of methane converter described for methane converter 36 can be used for methane converter 1036.

In vent mode 1046, the flow of gas from gas source 1022 can be directed so as to bypass all of flow meters 1026, 1028, methane detector 1034, and methane converter 1036 and exit from system 1020 via measurement exhaust 1032.

In some embodiments, system 1020 is installed at a vent for a methane source 1022. In some embodiments, the methane source 1022 is an ethylene glycol purifier, glycol dehydrator tower, compressor seal, pneumatic control, or solution gas tank. In some embodiments, the flow meters used in system 1020 are selected to be accurate at flow rate ranges that are relevant to the anticipated flow rate for the methane source with which system 1020 is to be used. For example, solution gas tanks may vent more than 300 m$^3$/day and therefore larger capacity flow rate meters than described with reference to system 20 would be used; surface casing vent flow values are typically in an ultra low flow rate range whereas solution gas tanks and other potential sources of methane may have higher flow rates.

For example, in some embodiments, methane source 1022 is a glycol dehydrator tower. In some embodiments, system 1020 is installed at a glycol dehydrator tower, for example, at a vent from same that emits a gas that may or does contain methane. In some embodiments, system 1020 is configured to detect and/or measure methane at methane detector 1034 and convert methane to another component at methane converter 1036 to monitor and/or minimize methane emissions from the glycol dehydrator tower.

As another example, in some embodiments, methane source 1022 is a compressor seal. In some embodiments, system 1020 is installed at compressor seal, for example, at a vent from same that may or does contain methane. In some embodiments, system 1020 is configured to detect and/or measure methane at methane detector 1034 and convert methane to another component at methane converter 1036 to monitor and/or minimize methane emissions from the compressor seal.

As another example, in some embodiments, methane source 1022 is a pneumatic control. In some embodiments, system 1020 is installed at a pneumatic control, for example, at a vent from same. In some embodiments, system 1020 is configured to detect and/or measure methane at methane detector 1034 and convert methane to another component at methane converter 1036 to monitor and/or minimize methane emissions from the pneumatic control.

As another example, in some embodiments, methane source 1022 is a surface casing vent at a wellhead, and system 1020 is used to monitor and/or minimize methane emissions from the wellhead in a manner similar to system 20 without being used to regulate any functions of the well such as shut-in or venting. In some embodiments, system 1020 is configured to detect and/or measure methane at methane detector 1034 and convert methane to another component at methane converter 1036.

As another example, in some embodiments, methane source 1022 is a solution gas tank. In some embodiments, system 1020 is installed at solution gas tank, for example at a vent associated with same. In some embodiments, system 1020 is configured to detect and/or measure methane at methane detector 1034 and convert methane to another component at methane converter 1036.

Figure 8:
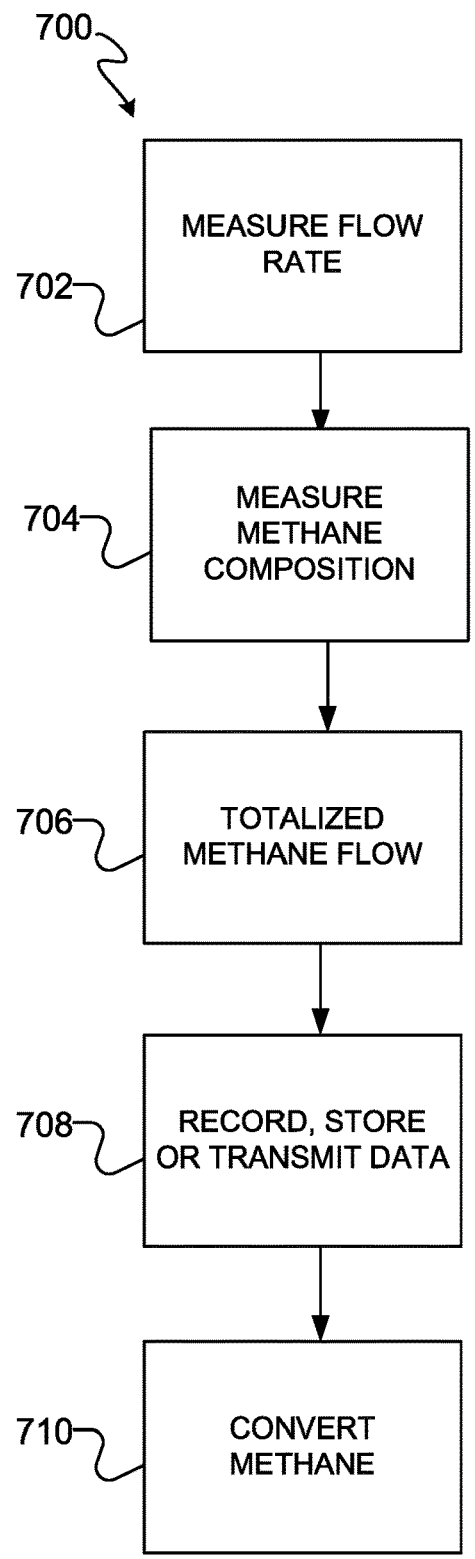
FIG. 8 shows an example embodiment of a method for measuring and converting methane according to an example embodiment.

FIG. 8 shows an example embodiment of a method 700 of using system 1020 to monitor and convert methane emissions from gas source 1022. At 702, the flow rate of gas emitted by gas source 1022 is determined, e.g. using flow meters 1026 and/or 1028.

At 704, the methane composition of gas emitted by gas source 1022 is determined, e.g. the percentage or proportion of the emitted gas that is methane is determined using methane detector 1034.

At 706, a totalized methane flow is determined, for example per unit volume of gas released by gas source 1022 or per unit time, or a total volume released within a given study period.

At 708, data pertaining to the flow rate, methane composition, and any other desired parameters measured by system 1020 is recorded, stored and/or transmitted, for example via logging memory 1040 and/or communications module 1058.

At 710, methane in the gas flow is converted to a different compound, for example carbon dioxide, using one or more methane converters 1036.

In some embodiments, system 20 or 1020 does not include a methane converter 36 or 1036 where the methane source 22 or 1022 is below a threshold size, emits gas below a threshold gas flow, or emits methane below a threshold methane amount or percentage in a gas flow. In some embodiments, system 20 or 1020 includes a methane converter 36 or 1036, for example, where methane source 22 or 1022 is above a threshold size, emits gas above a threshold gas flow, or emits methane above a threshold methane amount or percentage in a gas flow. In some embodiments, system 20 or 1020 includes a second methane detector positioned downstream of methane converter 36 or 1036, in order to evaluate what percentage of methane is converted to a different compound by methane converter 36 or 1036. As government regulations and pricing around the release of methane increase, it is anticipated that the threshold level of methane at which a methane converter is included as a component of the system will decrease.

In some embodiments, system 20 or 1020 is configured to output data confirming the amount of methane released from gas source 22 or 1022 over a given period of time, and the amount of methane that was diverted from being released to the atmosphere by reason of the use of methane converter 36 or 1036 to convert the methane to a different compound, for example carbon dioxide. Such information may be used by the operator of system 20 or 1020 for purposes such as internal monitoring, external reporting (e.g. to governments or regulatory agencies), claiming emissions credits, monitoring compliance with emissions regulations, or any other desired purpose.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

Although certain embodiments above have been described with reference to their use to monitor and/or convert methane released from a gas or oil well or certain other specifically described methane sources, other embodiments have application in other contexts. For example, landfills and other sources of decomposing organic matter (e.g. manure) may generate appreciable amounts of methane, and some embodiments could be used in such contexts to monitor, quantify and/or convert methane as described herein.

The invention claimed is:

1. A method for detecting methane emitted from a gas source, the method comprising:
   measuring a flow rate of gas released by the gas source, wherein measuring the flow rate of gas released by the gas source comprises measuring using a high flow rate range and measuring using a low flow rate range, wherein a first flow meter is used to conduct the step of measuring using the high flow rate range, and wherein a second flow meter is used to conduct the step of measuring using the low flow rate range, and the first flow meter is provided on a first flow path and the second flow meter is provided on a second flow path, and the first and second flow paths are separate;
   measuring a proportion of methane present in the gas;
   determining the flow rate or volume of methane being released based on both the measured flow rate and the measured proportion of methane present in the gas; and
   selecting the high flow rate range if the measured flow rate of gas released by the gas source is above a predetermined threshold, and selecting the low flow rate range if the measured flow rate of gas released by the gas source is below the predetermined threshold;
   wherein the step of measuring the flow rate of gas released by the gas source comprises actuating a switching valve to direct the flow of gas to be measured through the first flow path and initially measuring using the high flow rate range and determining the flow rate of gas released by the gas source; and
   if the flow rate of gas released by the gas source is below the predetermined threshold, the step of selecting the low flow rate range comprises actuating the switching valve to direct the flow of gas to the second flow path to be measured using the low flow rate range.

2. A method as defined in claim 1, further comprising logging at least one of the following parameters: the measured flow rate, the measured proportion of methane present in the gas, the flow rate of methane being released, or the volume of methane being released during a specific period of time.

3. A method as defined in claim 2, wherein said logging further comprises logging timestamp data together with the at least one selected parameter.

4. A method as defined in claim 3, further comprising converting at least a portion of the methane present in the gas to carbon dioxide.

5. A method as defined in claim 4, wherein the step of converting is carried out after the step of measuring the proportion of methane in the gas.

6. A method as defined in claim 1, wherein the step of selecting the low flow rate range comprises a system being used to carry out the method automatically actuating the switching valve to direct the flow of gas to be measured to the low flow rate range.

7. A method as defined in claim 1, further comprising measuring methane composition in the gas at a rate of at least seven measurements per second.

8. A method as defined in claim 1, further comprising generating totalized methane flow data based on the measured flow rate and the measured proportion of methane present in the gas.

9. A method as defined in claim 1, wherein the predetermined threshold is less than about 6 $m^3$/day.

10. A system for detecting methane emitted from a gas source, the system comprising:
    a flow meter in fluid communication with the gas source for measuring a flow rate of gas released by the gas source, the flow meter comprising:
       a first flow meter suitable for measuring a low flow rate of gas from the gas source; and
       a second flow meter suitable for measuring a high flow rate of gas from the gas source, the first flow meter being provided on a first flow path and the second flow meter being provided on a second flow path, and the first and second flow paths being separate; and
    a methane detector in fluid communication with the gas source for measuring a proportion of methane present in the gas; and
    a switching valve positioned to direct the flow of gas from the gas source to either the first flow meter or the second flow meter based on a measured flow rate of the gas from the gas source.

11. The system as defined in claim 10, further comprising a memory for storing data pertaining to the measured flow rate and the measured proportion of methane.

12. The system as defined in claim 10, further comprising a converter for converting methane to carbon dioxide, the converter being in fluid communication with the gas source and positioned downstream of the methane detector.

13. The system as defined in claim 12, further comprising a vent positioned to allow the gas released by the gas source to bypass the flow meter, the methane detector, and the converter.

14. The system as defined in claim 10, wherein the first and second flow meters are laminar flow meters.

15. The system as defined in claim 10, further comprising a controller for automatically actuating the switching valve based on the measured flow rate of the gas from the gas source.

16. A method for detecting methane emitted from a gas source, the method comprising:
    measuring a flow rate of gas released by the gas source using a high flow rate range and a low flow rate range, wherein a first flow meter is used to conduct the step of measuring using the high flow rate range, and wherein a second flow meter is used to conduct the step of measuring using the low flow rate range, and the first flow meter is provided on a first flow path and the second flow meter is provided on a second flow path, and the first and second flow paths are separate;
    selecting the high flow rate range if the measured flow rate of gas released by the gas source is above a predetermined threshold, and selecting the low flow rate range if the measured flow rate of gas released by the gas source is below the predetermined threshold;
    measuring a proportion of methane present in the gas; and
    providing both the measured flow rate and the measured proportion of methane present in the gas for use in determining the flow rate or volume of methane being released;
    wherein the step of measuring the flow rate of gas released by the gas source comprises actuating a switching valve to direct the flow of gas to be measured through the first flow path and initially measuring using the high flow rate range and determining the flow rate of gas released by the gas source; and if the flow rate of gas released by the gas source is below the predetermined threshold, the step of selecting the low flow rate range comprises actuating the switching valve to direct the flow of gas to the second flow path to be measured using the low flow rate range.

\* \* \* \* \*